United States Patent
Brand et al.

(10) Patent No.: US 10,300,239 B2
(45) Date of Patent: May 28, 2019

(54) DEVICE AND METHOD FOR ASSISTING A COUGH

(75) Inventors: Maarten Leonardus Christian Brand, Monroeville, PA (US); Sheng Jin, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1426 days.

(21) Appl. No.: 13/384,410

(22) PCT Filed: Jul. 20, 2010

(86) PCT No.: PCT/IB2010/053292
§ 371 (c)(1),
(2), (4) Date: Jan. 17, 2012

(87) PCT Pub. No.: WO2011/010279
PCT Pub. Date: Jan. 27, 2011

(65) Prior Publication Data
US 2012/0111329 A1    May 10, 2012

(30) Foreign Application Priority Data

Jul. 24, 2009 (CN) .......................... 2009 1 0161656

(51) Int. Cl.
*A61M 16/20* (2006.01)
*A61H 23/00* (2006.01)
(Continued)

(52) U.S. Cl.
CPC ........... *A61M 16/202* (2014.02); *A61H 23/00* (2013.01); *A61H 31/00* (2013.01);
(Continued)

(58) Field of Classification Search
CPC .............. A61M 16/00; A61M 16/0009; A61M 15/0051; A61M 2205/50; A61M 2205/33;
(Continued)

(56) References Cited

U.S. PATENT DOCUMENTS 3,683,655 A * 8/1972 White .................. A61H 9/0078
601/44
4,448,192 A    5/1984 Stawitcke
(Continued)

FOREIGN PATENT DOCUMENTS

WO    2007054829 A2    5/2007
WO    WO 2007054829 A2 *  5/2007 ............ A61M 16/00
(Continued)

*Primary Examiner* — Jan Christopher L Merene
*Assistant Examiner* — Elliott S Ruddie
(74) *Attorney, Agent, or Firm* — Michael W. Haas

(57) ABSTRACT

The invention provides a device (11) for assisting a cough, based on an oscillation pressure. The oscillation pressure causes a periodic oscillation airflow in a lung system and the periodic oscillation airflow comprises an oscillation exhalation airflow and an oscillation inhalation airflow. The device (10) comprises a controlling unit (11), and the controlling unit (11) comprises:
  a first determining unit (111) for determining whether an inhalation of the lung system is complete, so as to control a valve (13) which is to be closed for isolating the lung system from the external environment,
  a second determining unit (112) for determining whether an internal air pressure in the lung system is larger than a pre-defined pressure threshold, and
  a detecting unit (113) for detecting the start of the oscillation exhalation airflow, so as to control the valve (13) which is to be opened for starting a cough.

12 Claims, 4 Drawing Sheets

(51) Int. Cl.
*A61H 31/00* (2006.01)
*A61M 16/00* (2006.01)

(52) U.S. Cl.
CPC ...... *A61M 16/0006* (2014.02); *A61M 16/024* (2017.08); *A61H 2201/5007* (2013.01); *A61H 2201/5071* (2013.01); *A61M 16/204* (2014.02); *A61M 16/205* (2014.02); *A61M 2016/0027* (2013.01); *A61M 2016/0036* (2013.01)

(58) Field of Classification Search
CPC ..... A61B 5/087; A61B 5/0871; A61B 5/0873; A61B 5/0875; A61B 5/0876; A61B 5/0878; A61B 5/091; A61B 5/0823; A61B 5/0826; A61H 23/00; A61H 31/00; A61H 2201/5007; A61H 2201/5071
USPC ............ 128/204.21, 205.24, 205.19, 204.18, 128/204.23; 600/529, 530, 531, 532, 533, 600/534, 535, 536, 537, 538, 539, 540, 600/541, 542, 543
See application file for complete search history.

(56) References Cited

U.S. PATENT DOCUMENTS

| | | | |
|---|---|---|---|
| 4,838,263 A | 6/1989 | Warwick et al. | |
| 5,303,698 A * | 4/1994 | Tobia et al. | 128/204.21 |
| 5,551,420 A * | 9/1996 | Lurie | A61H 31/00 |
| | | | 128/205.13 |
| 5,611,336 A | 3/1997 | Page | |
| 5,692,498 A * | 12/1997 | Lurie | A61H 31/00 |
| | | | 128/204.18 |
| 5,769,797 A | 6/1998 | Van Brunt et al. | |
| 6,030,353 A | 2/2000 | Van Brunt | |
| 6,349,724 B1 * | 2/2002 | Burton et al. | 128/204.18 |
| 6,415,791 B1 | 7/2002 | Van Brunt | |
| 7,128,069 B2 | 10/2006 | Farrugia et al. | |
| 2001/0037071 A1 * | 11/2001 | Lingo, Jr. | A61B 5/085 |
| | | | 600/538 |
| 2002/0188332 A1 * | 12/2002 | Lurie | A61H 31/00 |
| | | | 607/48 |
| 2006/0213518 A1 * | 9/2006 | DeVries et al. | 128/204.21 |
| 2007/0044796 A1 | 3/2007 | Estes et al. | |
| 2007/0199566 A1 | 8/2007 | Be'eri | |
| 2008/0000477 A1 * | 1/2008 | Huster | A61B 34/25 |
| | | | 128/204.23 |
| 2008/0135044 A1 * | 6/2008 | Freitag | A61M 16/16 |
| | | | 128/200.26 |
| 2009/0078255 A1 | 3/2009 | Bowman et al. | |
| 2009/0306556 A1 * | 12/2009 | Hansen | A61H 31/004 |
| | | | 601/43 |
| 2010/0095965 A1 * | 4/2010 | Piper | A61M 16/0816 |
| | | | 128/205.24 |

FOREIGN PATENT DOCUMENTS

| | | |
|---|---|---|
| WO | 2008063966 A1 | 5/2008 |
| WO | 2009067554 A1 | 5/2009 |

\* cited by examiner

DEVICE AND METHOD FOR ASSISTING A COUGH

FIELD OF THE INVENTION

The invention relates to a device and a method for assisting a cough.

BACKGROUND OF THE INVENTION

In some medical conditions, such as, Chronic Obstructive Pulmonary Disease (COPD), Asthma, and Cystic Fibrosis (CF), an excessive volume of viscoelastic material, which is called lung mucus, may be built up in the lung of a patient. Excessive lung mucus is known to cause severe problems due to an increased chance of lung infections, declined lung function, reduced effect of inhaled medicine etc.

The removal of excessive lung mucus is therefore highly beneficial to the health status of a patient. Normally patients are instructed to cough in special ways (called directed cough) or breathe in special patterns (called Huffing), but both often do not result in the desired effect.

Currently, an oscillation device to assist a cough is provided for Cystic Fibrosis and Chronic Obstructive Pulmonary Disease patients in order to increase lung mucus clearance. The oscillation can be air oscillation pressure transmitted to a lung through a mouth for causing the airways of a lung to oscillate. The oscillation also can be mechanical oscillation pressure transmitted to a lung through the ribcage and muscles, like for example High Frequency Chest Wall Oscillations (HFCWO).

However, based on the current oscillation device, when oscillation is generated in the airways of a lung, a periodic oscillation airflow is generated, and the direction of the periodic oscillation airflow may be different from the direction of cough (exhalation) airflow during a cough, which may impede the cough.

SUMMARY OF THE INVENTION

An object of this invention is to provide a device for effectively assisting a cough.

The device for assisting a cough, based on oscillation pressure, comprises a controlling unit. The oscillation pressure causes a periodic oscillation airflow in a lung system and the periodic oscillation airflow comprises an oscillation exhalation airflow and an oscillation inhalation airflow. The controlling unit comprises:
 a first determining unit for determining whether an inhalation of the lung system is complete, so as to control a valve which is to be closed for isolating the lung system from the external environment,
 a second determining unit for determining whether an internal air pressure in the lung system is larger than a pre-defined pressure threshold, and
 a detecting unit for detecting the start of the oscillation exhalation airflow, so as to control the valve which is to be opened for starting a cough.

The advantage is that the device of the invention can assist a cough more effectively.

The invention also provides a method corresponding to the device for assisting a cough.

The invention further provides a computer program used in the method of assisting a cough.

Detailed explanations and other aspects of the invention will be given below.

DESCRIPTION OF THE DRAWINGS

The above and other objects and features of the present invention will become more apparent from the following detailed description considered in connection with the accompanying drawings, in which.

The same reference numerals are used to denote similar parts throughout the Figures.

DETAILED DESCRIPTION

Figure 1:
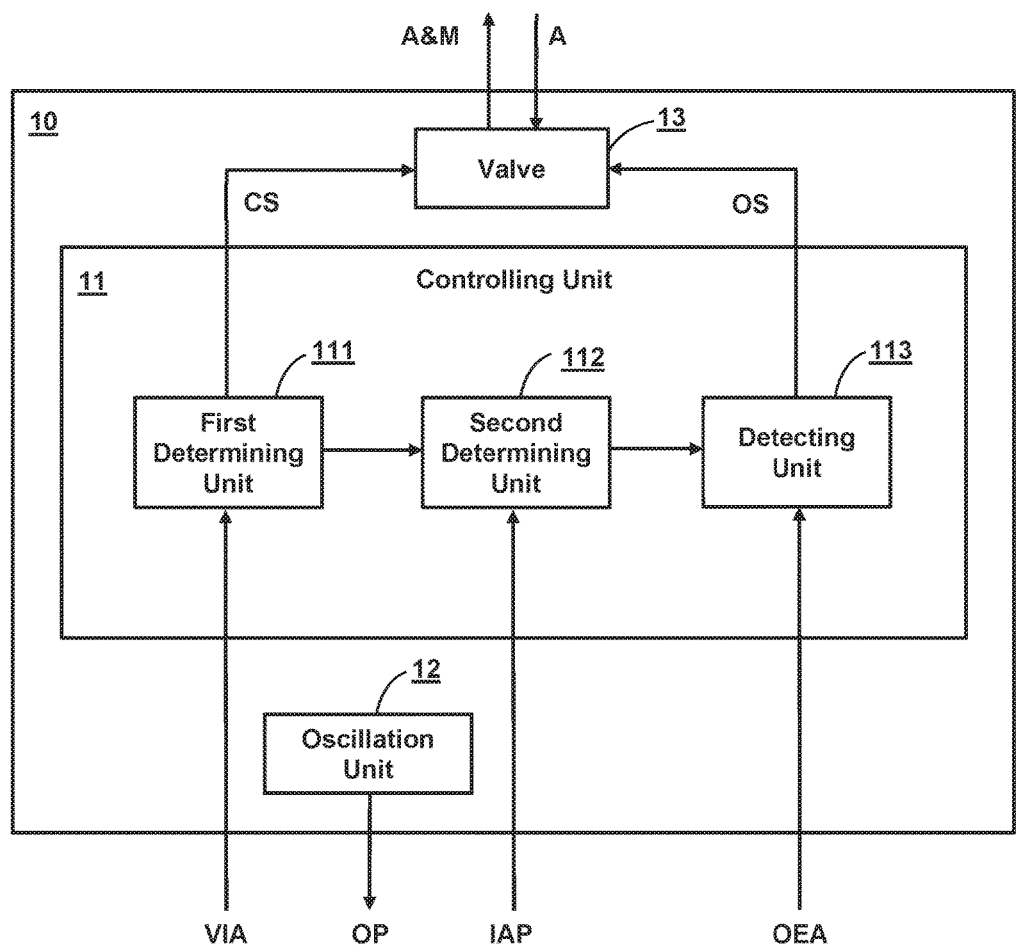
FIG. 1 schematically shows a device for assisting a cough according to an embodiment of the invention.

FIG. 1 schematically shows a device for assisting a cough according to an embodiment of the invention.

The device 10 is used for assisting a cough, based on an oscillation pressure. The device 10 comprises a controlling unit 11, an oscillation unit 12 for oscillating a lung system to cause a periodic oscillation airflow in the lung system, and a valve 13 controlled by the controlling unit 11, which valve is to be opened or closed for, respectively, connecting the lung system to the external environment through a mouth or isolating the lung system from the external environment.

The oscillation unit 12 may be integrated together with the controlling unit 11 and included in the device 10. For example, the oscillation unit 12 is an air oscillation pressure unit. The air oscillation pressure provided by the oscillation unit 12 is transmitted to the lung system through a mouth for causing the airways of a lung system to oscillate.

Alternatively, the oscillation unit 12 may be separate from the device 10, and not integral with the controlling unit 11. For example, the oscillation unit 12 is a mechanical pressure oscillation unit. The mechanical oscillation pressure is transmitted to the lung system through the ribcage and muscles, like for example High Frequency Chest Wall Oscillations (HFCWO).

The oscillation unit 12 generates an oscillation pressure (shown as OP in FIG. 1) to oscillate the airways of the lung system, and the oscillation pressure causes a periodic oscillation airflow in the airways of the lung system. The periodic oscillation airflow comprises an oscillation exhalation airflow and an oscillation inhalation airflow.

The controlling unit 11 comprises a first determining unit 111 for determining whether an inhalation of the lung system is complete, so as to control the valve which is to be closed for isolating the lung system from the external environment, a second determining unit 112 for determining whether an internal air pressure (shown as IAP in FIG. 1) in the lung system is larger than a pre-defined pressure threshold, and a detecting unit 113 for detecting the start of the oscillation exhalation airflow (shown as OEA in FIG. 1), so as to control the valve 13 which is to be opened for starting a cough.

The valve 13 may be integrated with the controlling unit 11 so as to be opened or closed based on the controlling action by the controlling unit 11. If the valve 13 is controlled so as to be closed based on a closing signal (shown as CS in FIG. 1) from the first determining unit 111, the lung system is isolated from the external environment and the external air cannot be inhaled into the lung system; if the valve 13 is controlled so as to be opened based on an opening signal (shown as OS in FIG. 1) from the detecting unit 113, mucus and air (shown as A&M in FIG. 1) in the airways of the lung system can be coughed/exhaled to the external environment, and external air (shown as A in FIG. 1) can be inhaled into the airways of the lung system.

When the internal air pressure of the lung system is larger than the pre-defined pressure threshold, the lung system is ready to cough; if the detecting unit 113 detects the start of the oscillation exhalation airflow, the valve 13 is controlled so as to be opened; if the valve 13 is open, the lung system starts to cough when the oscillation exhalation airflow starts according to the periodic oscillation airflow. The pre-defined pressure threshold may be set by a user, and the pre-defined pressure threshold may be different for different people.

The first determining unit 111 may be intended to determine whether the inhalation of the lung system is complete when the velocity of an inhalation airflow (shown as VIA in FIG. 1) in the lung system is lower than a pre-defined velocity threshold. The oscillation exhalation airflow is synchronous with the exhalation airflow of the cough at least at the beginning of the cough. At the beginning of the cough, the cough causes a peak exhalation airflow in the airways of the lung system. The pre-defined velocity threshold may be set by a manufacturer of the device 10 or a user, and the velocity threshold can be zero or any other value near zero.

The inhalation airflow may comprise the inhalation airflow caused by the inhalation of the lung system only. Alternatively, the inhalation airflow may comprise the inhalation airflow caused by the inhalation of the lung system and the oscillating inhalation airflow caused by the oscillation pressure.

The first determining unit 111 may comprise a sensor for collecting the velocity of inhalation air in airways of the lung system, and the second determining unit may comprise a sensor for collecting the internal air pressure of the lung system. Alternatively, the sensor of the first determining unit 111 may be integrated together with the sensor of the second determining unit 112.

Figure 2:
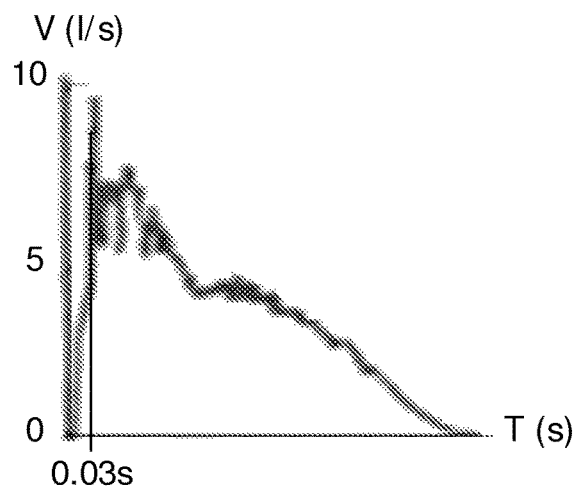
FIG. 2 is a diagram for illustrating a correlation between the velocity of an exhalation airflow of a cough and time.

FIG. 2 is a diagram for illustrating a correlation between the velocity of an exhalation airflow of a cough and time. At the beginning of a cough, for example, at 0.03 seconds, the velocity of the exhalation airflow is almost 10 l/s (liter/second).

Figure 3:
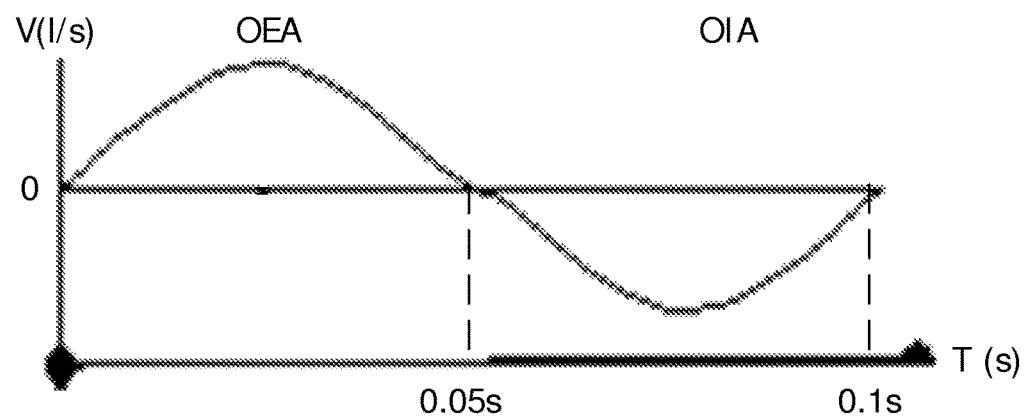
FIG. 3 is a waveform for illustrating a correlation between the velocity of an oscillation airflow and time.

FIG. 3 is a waveform for illustrating a correlation between the velocity of an oscillation airflow and time. The oscillation pressure causes a periodic oscillation airflow in the airways of the lung system, and the oscillation exhalation airflow of the oscillation airflow and the oscillation inhalation airflow of the oscillation airflow periodically change. In the first 0.05 s, the oscillation pressure causes an oscillation exhalation airflow (shown as OEA in FIG. 3) in the airways of the lung system, and in the next 0.03 s, the oscillation pressure causes an oscillation inhalation airflow (shown as OIA in FIG. 3) in the airways of the lung system. The period of the periodic oscillation airflow can be 0.1 s, 0.2 s, 0.3 s etc.

In an embodiment of the invention: firstly, the internal air pressure of the lung system is larger than the pre-defined pressure threshold, and the lung system is ready to cough; secondly, in a periodic oscillation airflow, an oscillation exhalation airflow starts; thirdly, the valve 13 is opened; fourthly, the lung system starts to cough and causes a peak exhalation airflow in the airways of the lung system at the beginning of the cough, for example, at 0.03 s, and, synchronously, in the periodic oscillation airflow, an oscillation exhalation airflow starts.

Figure 4:
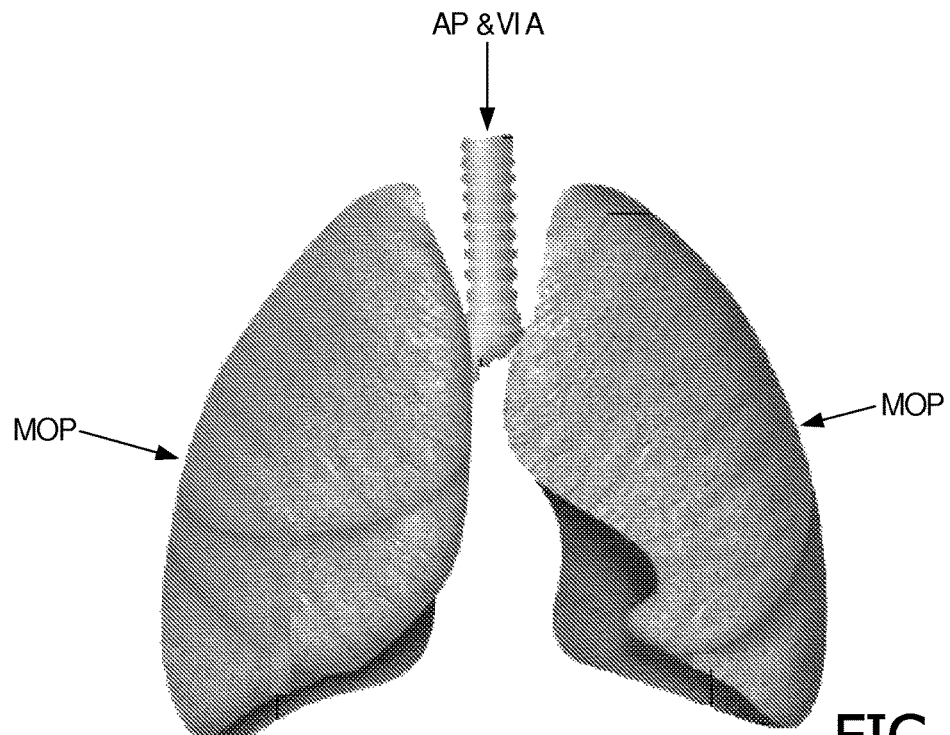
FIG. 4 schematically shows a mechanical oscillation pressure applied to a lung system and an air pressure detected through a mouth according to an example of the invention.

FIG. 4 schematically shows a mechanical pressure oscillation (shown as MOP) applied to a lung system, and an air pressure (shown as AP) in the lung system is detected through a mouth according to an example of the invention.

Figure 5:
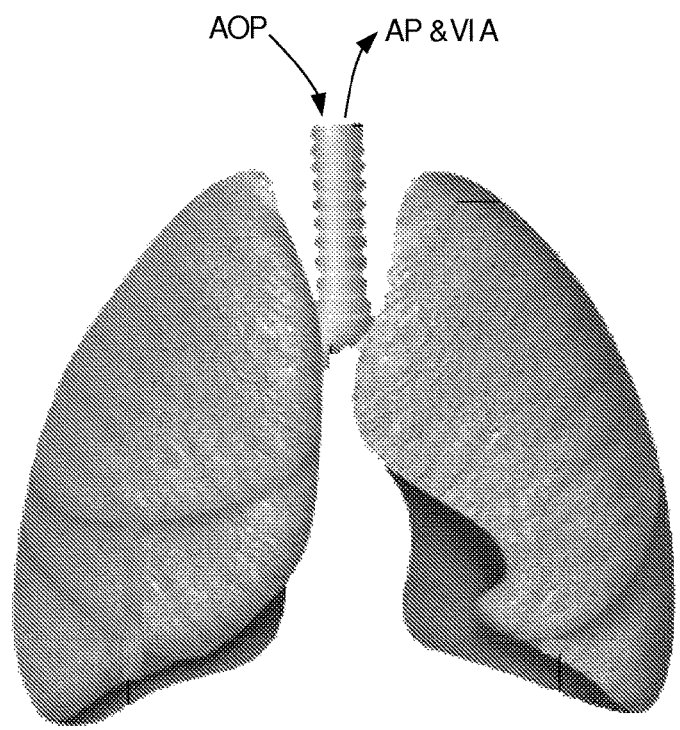
FIG. 5 schematically shows an air oscillation pressure applied to a lung system through a mouth and an air pressure detected through the mouth according to another example of the invention.

FIG. 5 schematically shows an air oscillation pressure (shown as AOP) applied to a lung system through a mouth, and an air pressure (AP) in the lung system is detected through the mouth according to another embodiment of the invention.

Figure 6:
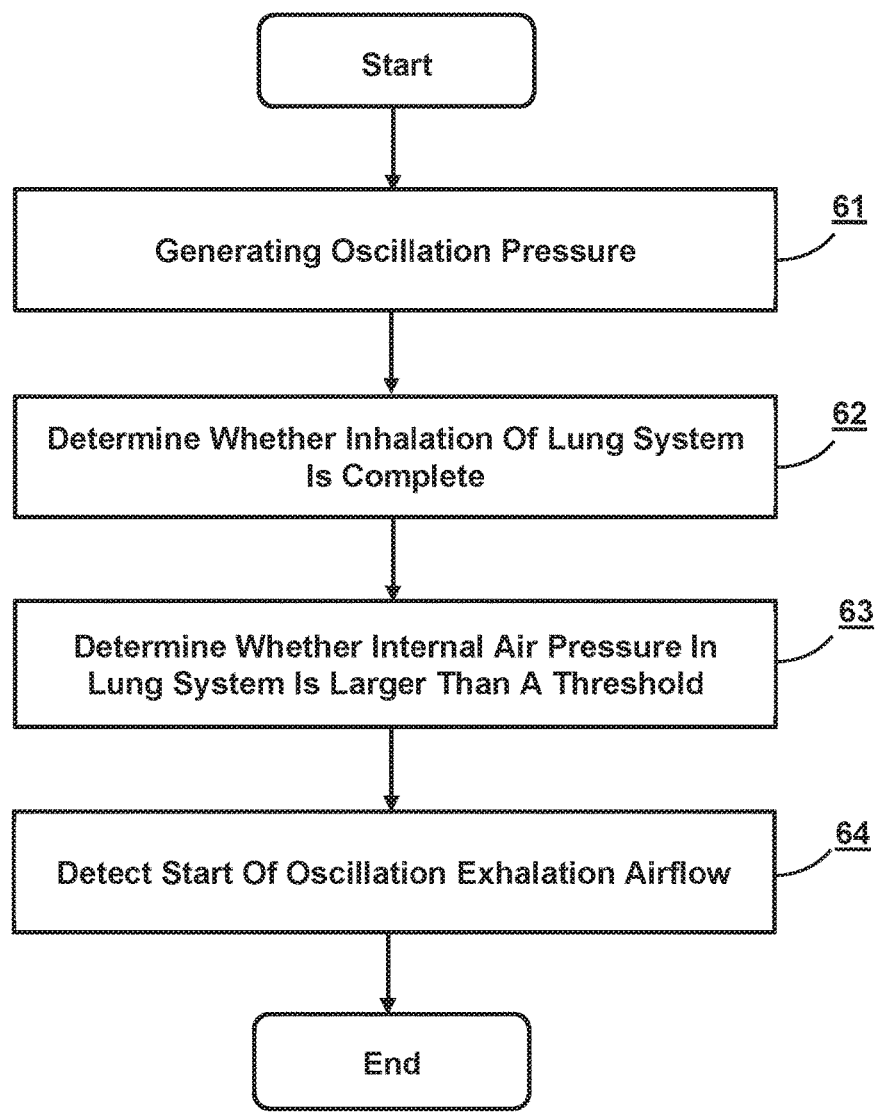
FIG. 6 is a flow chart for illustrating a method of assisting a cough according to an embodiment of the invention.

FIG. 6 is a flow chart for illustrating a method of assisting a cough according to an embodiment of the invention. The method serves to assist a cough, based on an oscillation pressure, and the oscillation pressure causes a periodic oscillation airflow in the airways of a lung system. The periodic oscillation airflow comprises an oscillation exhalation airflow and an oscillation inhalation airflow. The method comprises the following steps.

A step is carried out to determine 62 whether an inhalation of the lung system is complete, so as to control a valve 13 which is to be closed for isolating the lung system from the external environment. The determining step 62 is intended to determine whether the inhalation of the lung system is complete when the velocity of an inhalation airflow in the lung system is lower than a pre-defined velocity threshold.

A next step is carried out to determine 63 whether the internal air pressure in the lung system is larger than a pre-defined pressure threshold.

A following step is carried out to detect 64 the start of the oscillation exhalation airflow, so as to control the valve 13 which is to be opened for starting a cough. The oscillation exhalation airflow is synchronous with the exhalation airflow of the cough, at least at the beginning of the cough.

The method further comprises a step of generating 61 the oscillation pressure to oscillate the lung system so as to cause the periodic oscillation airflow in the airways of the lung system.

When the internal air pressure of the lung system is larger than the pre-defined pressure threshold, the lung system is ready to cough; in the periodic oscillation airflow, if an oscillation exhalation airflow starts, the valve 13 is controlled to open; if the valve 13 is open, the lung system starts to cough when an oscillation exhalation airflow starts according to the periodic oscillation airflow.

The determining step 62 may be intended to determine whether the inhalation of the lung system is complete when the velocity of an inhalation airflow in the lung system is lower than a pre-defined velocity threshold. The oscillation exhalation airflow is synchronous with the exhalation airflow of the cough, at least at the beginning of the cough The inhalation airflow may comprise the inhalation airflow caused by the inhalation of the lung system only. Alternatively, the inhalation airflow may comprise the inhalation airflow caused by the inhalation of the lung system and the oscillating inhalation airflow caused by the oscillation pressure.

A computer program used in the method of assisting a cough, based on an oscillation pressure, wherein the oscillation pressure causes a periodic oscillation airflow in a lung system and the periodic oscillation airflow comprises an oscillation exhalation airflow and an oscillation inhalation airflow, the method comprising the steps of:

determining 62 whether an inhalation of the lung system is complete, so as to control a valve (13) which is to be closed for isolating the lung system from the external environment, determining 63 whether an internal air pressure in the lung system is larger than a pre-defined pressure threshold, and detecting the start of the oscillation exhalation airflow, so as to control the valve which is to be opened for starting a cough.

The computer program used in the method of assisting a cough, the method further comprising a step of generating the oscillation pressure to oscillate the lung system, so as to cause the periodic oscillation airflow in the airways of the lung system.

The oscillation frequency corresponding to the oscillation pressure may be in a range of 10-20 Hz.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by a unit of hardware comprising several distinct elements and by a unit of a programmed computer. In the system claims enumerating several units, several of these units can be embodied by one and the same item of hardware or software. The use of the words first, second and third, et cetera, does not indicate any ordering. These words are to be interpreted as names.

The invention claimed is:

1. A device for assisting a cough comprising:
   a velocity sensor configured to detect a velocity of inhalation airflow in a lung system;
   a pressure sensor configured to detect an internal air pressure in the lung system;
   a valve configured to operate in one of an open state and a closed state, the valve facilitating airflow between the lung system and an external environment in the open state, and substantially preventing airflow between the lung system and the external environment in the closed state; and
   a processor configured to:
      determine whether an inhalation of the lung system is complete based on the detected velocity of inhalation airflow;
      control, in response to determining the inhalation of the lung system being complete, the valve to operate in the closed state;
      determine whether the detected internal air pressure in the lung system is larger than a pre-defined pressure threshold;
      control, in response to determining the internal air pressure being greater than the pre-defined pressure threshold, an oscillator to generate an oscillation pressure to oscillate the lung system and cause a periodic oscillation airflow in the lung system, the periodic oscillation airflow comprising an oscillation exhalation airflow and an oscillation inhalation airflow;
      control the valve to operate in the open state based on detecting a start of the oscillation exhalation airflow, and
      control the oscillation exhalation airflow to be synchronous with an exhalation of the cough.

2. The device as claimed in claim 1, wherein the processor is configured to determine whether the inhalation of the lung system is complete based on the detected velocity of the inhalation airflow in the lung system being lower than a pre-defined velocity threshold.

3. The device as claimed in claim 1, wherein the oscillator provides the oscillation pressure to oscillate the lung system by transmitting mechanical oscillation pressure through a ribcage and muscles surrounding the lung system via high frequency chest wall oscillations.

4. A method of assisting a cough with an assistance system comprising a valve that operates in one of a closed state and an open state, a velocity sensor, a pressure sensor, an oscillator, and a processor, the method comprising:
   detecting by the velocity sensor, a velocity of inhalation airflow in a lung system;
   detecting by the pressure sensor, an internal air pressure in the lung system;
   determining by the processor, whether an inhalation of the lung system is complete based on the detected velocity of inhalation airflow;
   controlling, in response to the inhalation of the lung system being complete, the valve to operate in the closed state, the valve substantially preventing airflow between the lung system and the external environment in the closed state;
   determining by the processor, whether the detected internal air pressure in the lung system is larger than a pre-defined pressure threshold;
   generating by the oscillator, in response to the internal air pressure being greater than the pre-defined pressure threshold, an oscillation pressure to oscillate the lung system and cause a periodic oscillation airflow in the lung system, the periodic oscillation airflow comprising an oscillation exhalation airflow and an oscillation inhalation airflow;
   controlling the valve to operate in the open state based on detecting a start of the oscillation exhalation airflow; and
   controlling by the processor, the oscillation exhalation airflow to be synchronous with an exhalation of the cough.

5. The method as claimed in claim 4, wherein the processor determines whether the inhalation of the lung system is complete based on the detected velocity of the inhalation airflow in the lung system being lower than a pre-defined velocity threshold.

6. The method as claimed in claim 4, wherein generating the oscillation pressure to oscillate the lung system comprises transmitting mechanical oscillation pressure through a ribcage and muscles surrounding the lung system via high frequency chest wall oscillations.

7. A non-transitory computer readable medium including computer executable instructions, wherein the instructions, when executed by a computer, cause the computer to perform a method of assisting cough, the method comprising:
   detecting by a velocity sensor, a velocity of inhalation airflow in a lung system;
   detecting by a pressure sensor, an internal air pressure in the lung system;

determining by a processor, whether an inhalation of the lung system is complete based on the detected velocity of inhalation airflow;

controlling by the processor, in response to the inhalation of the lung system being complete, the valve to operate in the closed state, the valve substantially preventing airflow between the lung system and the external environment in the closed state;

determining by the processor, whether the detected internal air pressure in the lung system is larger than a pre-defined pressure threshold;

generating by an oscillator, in response to the internal air pressure being greater than the pre-defined pressure threshold, an oscillation pressure to oscillate the lung system and cause a periodic oscillation airflow in the lung system, the periodic oscillation airflow comprising an oscillation exhalation airflow and an oscillation inhalation airflow;

controlling the valve to operate in the open state based on detecting a start of the oscillation exhalation airflow; and controlling by the processor, the oscillation exhalation airflow to be synchronous with an exhalation of the cough.

8. The computer readable medium as claimed in claim 7, wherein generating the oscillation pressure to oscillate the lung system comprises transmitting mechanical oscillation pressure through a ribcage and muscles surrounding the lung system via high frequency chest wall oscillations.

9. The device as claimed in claim 1, wherein a peak of the exhalation airflow occurs within a time period of the oscillation exhalation airflow.

10. The device as claimed in claim 1, wherein the periodic oscillation airflow is different than the inhalation airflow in the lung system.

11. The device as claimed in claim 1, wherein a time period of the oscillation exhalation airflow is greater than a time period of the oscillation inhalation airflow.

12. The device as claimed in claim 1, wherein the oscillation pressure is directly applied to the lung system.

* * * * *